(12) United States Patent
Giudiceandrea

(10) Patent No.: US 8,218,722 B2
(45) Date of Patent: Jul. 10, 2012

(54) METHOD FOR SCANNING THE INTERNAL QUALITY OF WOODEN ELEMENTS HAVING A MAIN DIRECTION OF EXTENSION, SUCH AS LOGS OR PLANKS

(75) Inventor: Federico Giudiceandrea, Bressanone (IT)

(73) Assignee: Microtec S.R.L., Bressanone (IT)

( * ) Notice: Subject to any disclaimer, the term of this patent is extended or adjusted under 35 U.S.C. 154(b) by 168 days.

(21) Appl. No.: 12/882,840

(22) Filed: Sep. 15, 2010

(65) Prior Publication Data

US 2011/0069811 A1   Mar. 24, 2011

(30) Foreign Application Priority Data

Sep. 21, 2009   (IT) ................. VR2009A0146

(51) Int. Cl.
*H05G 1/60*   (2006.01)
(52) U.S. Cl. ........................... 378/21; 378/58
(58) Field of Classification Search ............... 378/21, 378/58, 57, 62
See application file for complete search history.

(56) References Cited

U.S. PATENT DOCUMENTS

| | | | |
|---|---|---|---|
| 5,023,805 A | | 6/1991 | Aune et al. |
| 6,157,698 A | * | 12/2000 | Pietikainen et al. ............ 378/58 |
| 6,757,354 B2 | * | 6/2004 | Skatter et al. .................... 378/58 |
| 2002/0080914 A1 | * | 6/2002 | West et al. ....................... 378/58 |
| 2002/0168083 A1 | | 11/2002 | Garms et al. |
| 2005/0190958 A1 | | 9/2005 | Woods et al. |

FOREIGN PATENT DOCUMENTS

WO   02/091286 A2   11/2002

OTHER PUBLICATIONS

Seger Maria Magnusson et al., "Scanning of logs with linear cone-beam tomography", Computers and Electronics in Agriculture, Elsevier Science B.V., doi:10.1016/S0168-1699(03)00041-3, vol. 41, No. 1-3, Dec. 1, 2003, pp. 45-62, XP007909039, ISSN: 0168-1699.

* cited by examiner

*Primary Examiner* — Irakli Kiknadze
(74) *Attorney, Agent, or Firm* — Pearne & Gordon LLP

(57) ABSTRACT

A method for scanning the internal quality of wooden elements (1) such as logs or planks comprises the operating steps of irradiating the wooden element (1) with at least one beam (3) of electromagnetic radiation according to one or more directions of irradiation which are transversal to the main axis of extension, at the same time creating a relative helicoidal movement between the wooden element (1) and the beam (3). During the movement, for a plurality of separate reciprocal positions of the wooden element (1) and the beam (3), the residual intensity of the electromagnetic radiation which passed through the wooden element (1) is detected for a detection length (L). The relative movement is created in such a way that the helix has a pitch P equal to Y times the sum of the detection length (L) of all of the detectors used, where $Y \geq 5$. Moreover, reconstruction of the internal structure of the wooden element (1), at a cross-section of it, is at least implicitly performed by dividing the volume of the wooden element (1), at the section to be reconstructed, into a plurality of basic volumes having a dimension along the main axis of extension which is equal to at least X times the detection length (L) of each detector used, where $X \geq 5$.

20 Claims, 6 Drawing Sheets

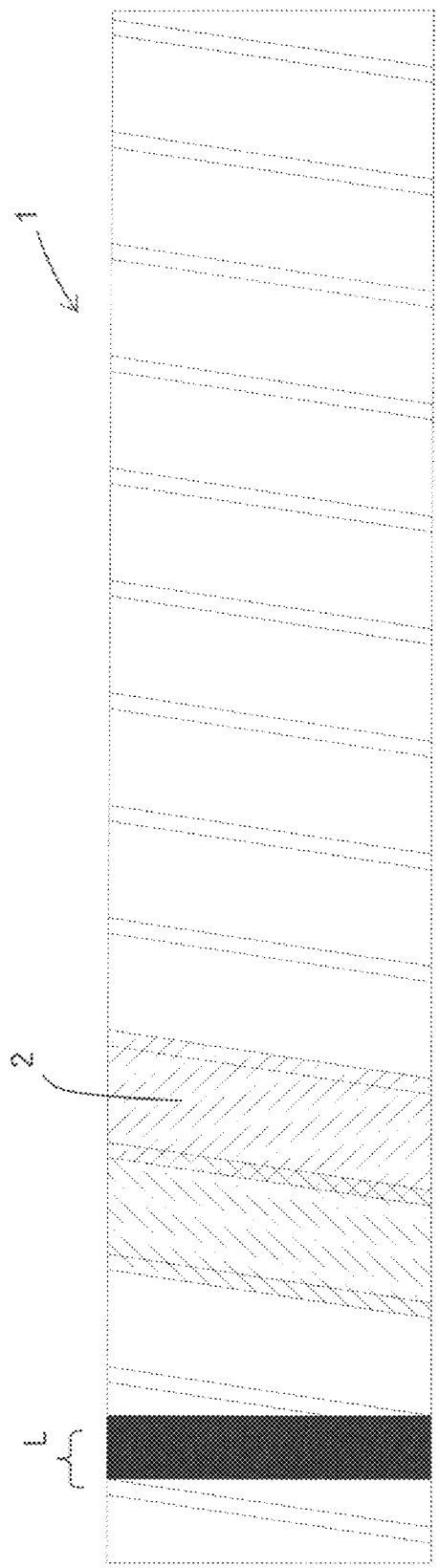

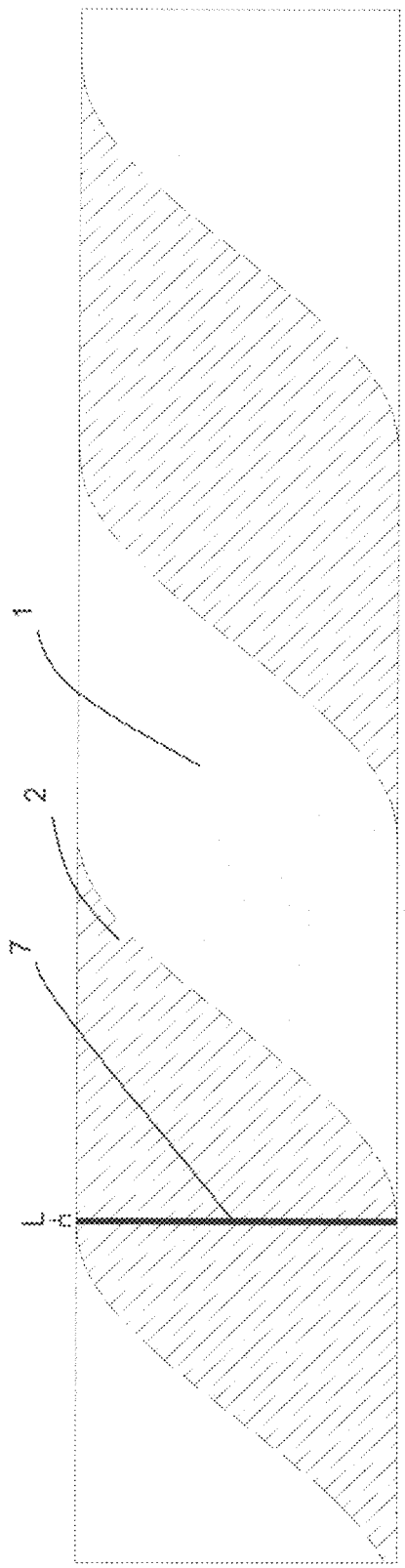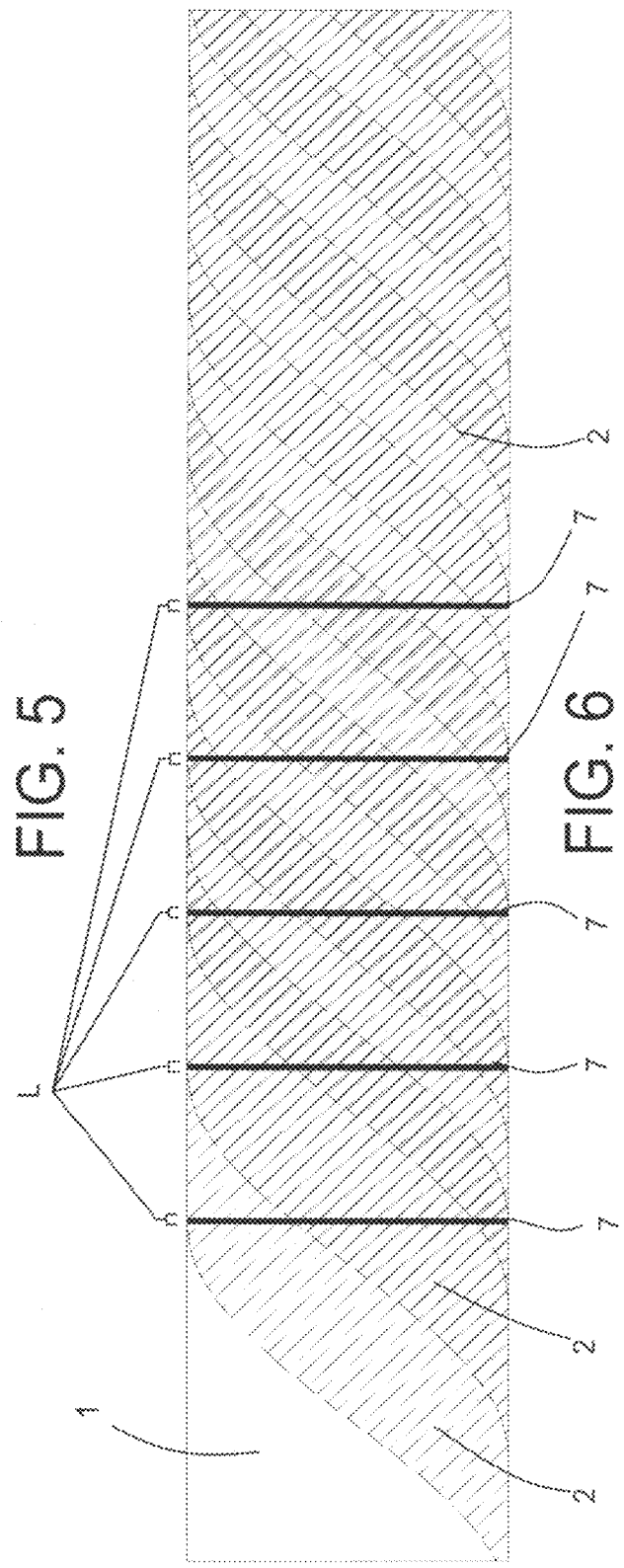

METHOD FOR SCANNING THE INTERNAL QUALITY OF WOODEN ELEMENTS HAVING A MAIN DIRECTION OF EXTENSION, SUCH AS LOGS OR PLANKS

This invention relates to a method for scanning the internal quality of wooden elements having a main direction of extension, such as logs or planks (since, in any case, the main application relates to logs, hereinafter, in order to provide a simple description, reference is frequently made only to them).

In particular, this invention relates to detecting those aspects of wooden elements which remain practically constant over a significant part of the wooden elements, such as cracks, decaying zones, growth rings, bark, etc. At present, there are two main systems for scanning the internal quality of logs: the rotary tomograph system and the multiple fixed sources system. In the former, the tomograph rotates about the log (approximately about its main axis) and each transversal "slice" of the log is subjected to a plurality of readings according to different angular positions (normally in order to obtain good information readings must be repeated for just over half a revolution about the log). Each slice is selected with a width equal to that of the electromagnetic beam and substantially equal to the width of the corresponding detector. Moreover, in general, the tomograph detector is a matrix detector having one or more rows of sensors (the rows of sensors extend transversally to the main axis and are arranged alongside each other along the main axis). Consequently, each slice of the log analyzed is divided into one or more basic slices, each of which has a width substantially equal to the width of a row of detection sensors.

The reconstruction of the appearance of the section of the slice is created using known algorithms described in detail in scientific literature and therefore not referred to in further detail herein.

The resolution of the information obtained depends on the dimensions of the sensors (in inverse proportion), the number of sensors (proportionally) and the number of readings taken.

In the known way, the tomographic reconstruction is created by virtually dividing the volume of the slice being examined into a plurality of basic volumes where the density is assumed to be constant. Each volume has a dimension in the plane in which the beam of electromagnetic radiation lies which depends on the number of sensors, their size and the number of readings, and a length equal to the width of the respective row of sensors.

Moreover, in practice, to speed up detection operations, tomograph rotation is simultaneous with log feed. The two movements are synchronized in such a way that each basic volume is detected by at least one sensor for the required number of different angular positions. That situation is schematically illustrated in FIG. 4 which shows a side view of a log on which the instantaneous position of the electromagnetic beam detected (black rectangle) and the helixes described by the projection of the beam detected on the surface of the log are marked. The two hatched areas also indicate the width of the helix and show how with each revolution the zones detected overlap to some extent.

Rotary tomographs therefore allow a high level of resolution of details to be obtained, but require very lengthy scan times for examining an entire log slice by slice.

The second system currently used (described for example in U.S. Pat. No. 5,023,805) again involves analyzing the log slice by slice, but using a plurality of fixed sources (and corresponding detectors) which are distributed around the log.

In this case, operation is similar to that of a rotary tomograph, for each slice of log taking a number of readings equal to the number of fixed sources, upon reaching the angular position corresponding to each of them.

This system is extremely fast but has less than optimum resolution, since it allows only several types of very local defects to be detected. In particular, this system is not able to detect the presence of cracks in the log. Said defect can be detected by means of a tomographic scan only if observed in the plane in which it extends, whilst it is practically invisible if observed in the transversal direction (because of its very limited thickness the difference in attenuation of the electromagnetic radiation is practically negligible compared with a log which has no crack).

In the medical sector, very rapid rotary tomographs are built which use the cone-beam technique, using very large matrices of sensors so as to be able to advance rapidly. This technique is schematically illustrated in FIG. 2, which shows a log-shaped body, an emitter, a flat sensor, the cone-shaped beam and the image of the body. Suitable algorithms allow the image to be deciphered, compensating for the different angle (and therefore the different quantity of material passed through) of the beams detected by the various rows of sensors.

However, this technique is also not without disadvantages, since the costs are very high for production of the sensors and for transmission and processing of the data acquired.

In contrast, FIG. 1 shows the fan beam technique (also in some cases used in the timber sector) in which the electromagnetic beam is perpendicular to the axis of the log and has a limited thickness. In FIG. 1 the detector extends substantially in a linear fashion.

In this situation, the technical purpose which forms the basis of this invention is to provide a method for scanning the internal quality of wooden elements having a main direction of extension which overcomes the above-mentioned disadvantages.

In particular, this invention aims to provide a method able to detect, at high speeds, features (defects, but not only defects) which cannot be detected using conventional fixed source systems, but which at the same time has production and operating costs comparable with those of fixed source systems.

In particular, the technical purpose of this invention is to provide a method for scanning the internal quality of wooden elements having a main direction of extension, which allows a view of those particular features that remain constant over a significant part of the log, such as cracks and decaying zones.

The technical purpose specified and the aims indicated are substantially achieved by a method for scanning the internal quality of wooden elements having a main direction of extension as described in the appended claims.

Further features and the advantages of this invention are more apparent from the detailed description of several preferred, non-limiting embodiments of a method for scanning the internal quality of wooden elements having a main direction of extension described below with reference to the accompanying drawings, in which:

FIG. 4 is a schematic side view of a log on which the trend of a prior art rotary tomograph detection technology (described above) is represented;

FIG. 5 is a schematic side view of a log on which the trend of a second embodiment this invention is represented;

FIG. 6 is a schematic side view of a log on which the trend of a third embodiment this invention is represented;

Figure 1:
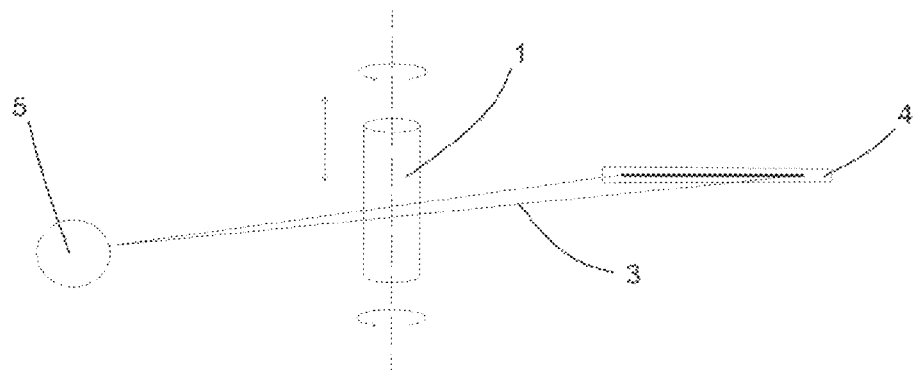
FIG. 1 is a schematic illustration of a first prior art detection technique (described above)
Figure 2:
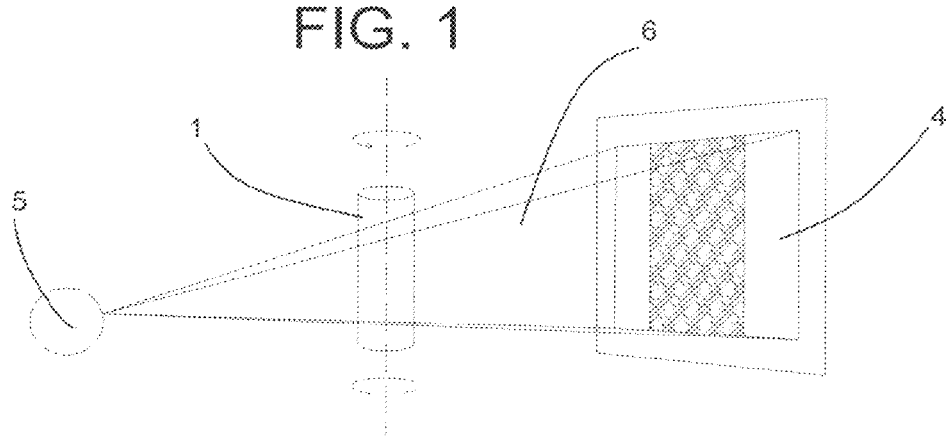
FIG. 2 is a schematic illustration of a second prior art detection technique (described above)

Hereinafter the reference numbers identifying aspects shared by this invention and by the prior art also appear in FIGS. 1, 2 and 4.

The method for scanning the internal quality of wooden elements 1 having a main direction of extension, such as logs or planks, according to this invention is a method based on a tomographic reconstruction of the wooden element 1 allowing identification not so much of local defects, but above all of the features of the wooden element 1 which remain substantially the same over a predetermined axial length. In other words, the method according to this invention uses a combination of tomographic readings and a priori information, that is to say, the information that several features of a wooden element 1 extend in substantially the same way over a predetermined axial length. Consequently, if for example the same feature (such as a crack, a growth ring, etc.) is detected as substantially the same in two cross-sections (relative to the main axis of extension) spaced from each other, it may reasonably be assumed that it is substantially the same over the entire stretch of the wooden element 1 between the two portions detected.

The embodiment proposed in this invention is therefore substantially that of performing a wide-helix 2 rotary tomographic scan, that is to say, a rotary tomographic scan in which each transversal slice of the wooden element 1 is detected a limited number of times, fewer than the minimum number for a conventional tomographic reconstruction. The term helix 2 refers to the projection on the surface of the log of the images of it which are gradually detected. Whilst in conventional rotary tomograph solutions said projection covers the entire lateral surface of the log (overlapping in several cases—FIG. 4), in this invention it only covers a band whose width is comparable to that of the band not covered by the projections (FIG. 5). Consequently, whilst in the prior art rotary tomograph technique each point of the volume of the wooden element 1 is detected according to a plurality of different directions distributed over a relatively large angle (around 180°), in the method according to this invention each point of the volume is only detected a few times for an overall angle which may even be very small (about a few degrees). In order to be able to obtain the tomographic reconstruction, the method according to this invention in contrast requires the use for each point of the readings obtained according to other angles of rotation for the points axially aligned with it (described in more detail below) for covering the detection angle required by the reconstruction algorithms.

In accordance with this invention, the method comprises in general a first operating step of taking a wooden element 1 having a main direction of extension that can be identified with its main axis of extension.

The wooden element 1 is then irradiated with at least one beam 3 of electromagnetic radiation in one or more directions of irradiation which are transversal to the main axis of extension (the structure of the beam 3 is described in more detail below).

Associated with the beam 3 there is at least one detector 4 comprising a plurality of sensors (the term sensors here indicating each basic detection cell) positioned on the opposite side of the wooden element 1 to the point where the generator of the beam 3 of radiation is located. The detector 4 is designed to detect the residual intensity of at least part of the electromagnetic radiation which passed through the wooden element 1. Advantageously, the detector comprises a single row of sensors transversal to the log direction of feed (although, in some embodiments, the detector may also comprise two or more rows of sensors arranged side by side).

The overall width (or thickness), measured parallel with the main axis of extension, of the part of the beam 3 detected by each detector 4 is hereinafter indicated as the detection length L (defined "length" because it is measured along the main axis of extension of the wooden element 1). It should also be noticed that if the beam 3 consists of parallel electromagnetic radiation the detection width is irrespective of the measuring point, but if the beam 3 consists of diverging radiation, the detection width increases away from the point of beam 3 emission. In this case, hereinafter, the detection length L is the average in the zone in which the radiation passes through the wooden element 1.

For example, FIG. 5 shows the case of a detector 4 advantageously consisting of a one-dimensional matrix of sensors (a single row of aligned sensors).

The above also indicates that, depending on the embodiments, the shape and dimensions of the beam 3 may vary. In particular, each beam 3 may be generated in such a way that it covers the wooden element 1, transversally to its main axis of extension, either completely (as in FIG. 5) or only partly. In the latter case, not illustrated, the beam 3 does not cover the entire width of the wooden element 1 (transversally to its main axis of extension) but only a smaller part of it. Moreover, depending on requirements, each beam 3 may cover a different thickness of the wooden element 1 (measured parallel with the main axis of extension).

However, advantageously, in the presence of a single beam 3, its width may be generated in such a way that it corresponds to the width of the respective detector 4.

Between the wooden element 1 and the beam 3 of electromagnetic radiation a relative helicoidal movement is created, having a first component which is a translation substantially parallel with the main axis of extension of the wooden element 1 and a second component which is a rotation substantially about the wooden element 1. In the preferred embodiment, the relative movement is generated by feeding the wooden element 1 (relative to the ground) in a direction of feed parallel with its main axis of extension, and at the same time rotating (again relative to the reference provided by the ground) each beam 3 and each detector 4 associated with it about the wooden element 1. Aside from said rotation, each beam 3 and each detector 4 is kept stationary (again relative to the ground). Advantageously, the helicoidal motion is also even.

As already indicated, in accordance with this invention the relative motion must be of the wide-helix type 2. In practice, this is achieved by ensuring that the helix defined by the relative movement has a pitch P equal to at least Y times the sum of the detection lengths L of the detectors used, where $Y \geq 5$. The meaning of said choices is described below. However, in the preferred embodiment $Y \geq 10$, and in the more preferred embodiments $Y \geq 20$.

The method according to this invention comprises detecting the residual intensity of the electromagnetic radiation a plurality of times during the helicoidal movement. In that way, each reading is taken with the wooden element 1 and the beam 3 (as well as the respective detector 4) in a different position relative to each other. Each reading will therefore be taken for a specific angular position and will correspond to a different stretch of the wooden element 1 (in the axial direction) relative to those of the other readings.

With reference to the case in which a single detector is used (FIG. 5), since, as already indicated, the relative movement of the wooden element 1, the beam 3 of radiation and the respective detector 4 is performed in a helix 2 with a pitch P at least Y times greater than the sum of the detection lengths L (which with a single detector corresponds to the single detection length L), each point of the wooden element 1 is only detected a few times according to directions of observation which are distributed on a covering angle that is limited and advantageously significantly less than the angle normally necessary for tomographic reconstruction in a rotary tomograph (normally equal to around half a revolution).

Therefore, with a single detector the precise number of readings and the relative covering angle for each point depend on the detection length L (in m) of the detector 4 (that is to say, the number of rows of sensors and their relative width), the speed of the first component V (in m/s) and of the second component G (in revolutions/s or °/s or rad/s) of the helicoidal motion, and the number of readings N taken per second. In particular, they can be calculated with the formulas:

$$\text{number of readings} = N \cdot L / V$$

$$\text{detection angle} = G \cdot L / V.$$

Moreover, since the pitch P is equal to V/G, and is equal to at least Y times the detection length (which, to a first approximation, is substantially equal to the length L), it may be deduced that the detection angle of each point of the wooden element 1 is not greater than 1/Y of a revolution.

Although said detection angle is less than that required by the typical reconstruction methods of the rotary tomograph (whether they are precise or approximate), in this invention it may be used thanks to the a priori information regarding the structure of the features being investigated.

Once the readings have been taken, the method according to this invention comprises reconstructing the internal structure of the wooden element 1 based on processing of the intensities detected for each reciprocal position of the wooden element 1 and the beam 3—detector 4 pairs.

To obtain this result, in accordance with this invention, the step of reconstructing the internal structure of the wooden element 1 (at a section of it transversal to the main axis of extension), is based on the set of information relating to that section and the information relating to the sections adjacent to it (on one side only or on both sides).

The reconstructing step is at least implicitly performed by considering the volume of the wooden element 1, at the section to be reconstructed, divided into a plurality of basic volumes (assumed to have constant density), each having a clearly extended structure parallel with the main axis of extension. In particular, each basic volume is identified in such a way that its dimension along the main axis of extension is equal to at least X times the detection length L of each detector used, where $X \geq 5$.

However, in the preferred embodiments, the value of the parameter X is linked to the parameter Y by the formula:

$$X = K \cdot Y$$

where K is the fraction of round angle that the reconstruction algorithm requires to be covered by the various readings (in the most common embodiments K is between 0.5 and 1).

This embodiment substantially corresponds to virtually widening the various readings, as if each reading were effectively representative of the entire piece of the wooden element 1 extending axially as much as the basic volumes, whilst in reality each reading axially relates to only part of the basic volumes.

As regards the other dimensions of each basic volume (in the plane perpendicular to the main axis of extension), in the known way they are determined by the resolution of the detector 4 (that is to say, by the size of the individual sensors of which it consists).

It should also be noticed that in the preferred embodiments in which the common reconstruction algorithms are used, identification of the basic volumes is only theoretical and implicit, and derives from the application, to readings which in reality are axially spaced, of formulas designed to be applied to readings which all lie in the same plane.

Therefore, as indicated, the reconstructing step is at least implicitly carried out by considering for each basic volume a plurality of readings taken through portions of the wooden element 1 which are at least partly separate and distributed along a stretch of the main axis of extension. In particular, said portions may be either partly axially overlapping or spaced in such a way that they are separated by a predetermined distance (that depends on the parameters used during implementation of the method).

In a more complex alternative embodiment of this invention the irradiation step is carried out by sending through the wooden element 1 a plurality of beams 3 of electromagnetic radiation (which advantageously are in a fixed position relative to each other), and the detection step is performed, for each reciprocal position of the wooden element 1 and the various beams 3, for each of the beams 3 of electromagnetic radiation.

Moreover, depending on requirements, the irradiation step may comprise the formation of a plurality of beams 3 which are parallel with each other, or of a plurality of beams 3 diverging from a single emitter 5. However, in any case the beams 3 are advantageously spaced in the direction of the main axis of extension at least at the moment when they pass through the wooden element 1.

In the case of parallel beams 3, the beams 3 may also extend in the same direction (with reference to the direction of propagation of the electromagnetic radiation) or they may have directions of propagation which are set at angles relative to each other, that is to say, orientated according to different angular positions relative to the main axis of extension. In the former case the detection step may be carried out by means of a plurality of detectors 4 arranged side by side and spaced out parallel with the main axis of extension, whilst in the latter case the various detectors 4 must be in different angular positions around the wooden element 1 (each on an opposite side of the wooden element 1 relative to the position of the respective detector 4).

Figure 3:
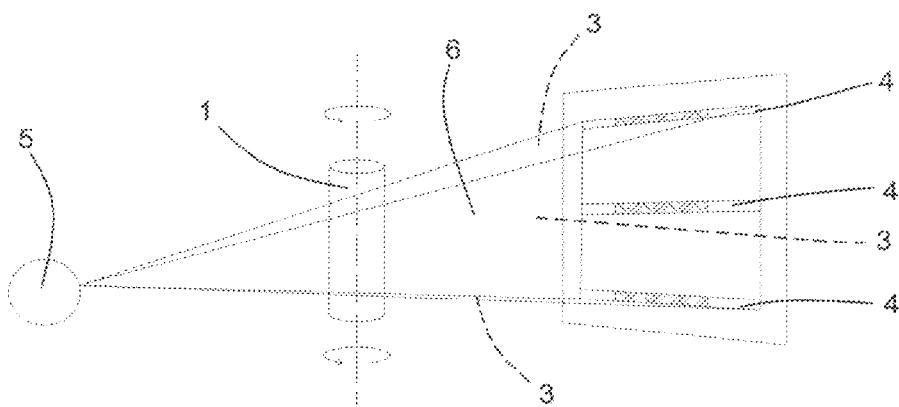
FIG. 3 is a schematic illustration of a detection technique which can be used in the method according to this invention.

Even in the case of diverging beams 3 (preferred embodiment since it can be implemented with a single emitter 5 of electromagnetic radiation), the detection step may be performed by means of a plurality of detectors 4 which are arranged side by side and spaced out parallel with the main axis of extension. Moreover, in the preferred embodiment, the diverging beams 3 are created by irradiating the wooden element 1 with a macro-beam 6 having the shape of a cone or a pyramid, that is to say, with a macro-beam 6 similar to that currently used in cone beam technology (FIG. 2), and detecting only portions of said macro-beam 6 as schematically illustrated in FIG. 3.

The embodiment illustrated in FIG. 6 shows an example of implementation of the method according to this invention in its most complex form. As can be seen, there are five detectors 4 present (and five corresponding beams 3) having a substantially linear extension and spaced axially by one fifth of the pitch P. That layout allows substantially the entire surface of the wooden element 1 to be covered with five different helixes which are partly overlapping (in the accompanying drawings the various helixes 2 are shown with a respective hatched portion and are completely represented only to the right of the respective detector 4 whose detection length is represented by the respective linear projection 7). Therefore, said solution would be preferable compared with a solution in which the detectors 4 were drawn near each other, since that would not allow the entire surface to be covered (and therefore would give a more limited angle of observation). Therefore, in the embodiment in FIG. 6 each cross-section of the log is detected from a limited number of points of views—angles (similarly to what happens in tomographs with multiple fixed sources), but combining the readings of two or more adjacent sections (obtained from two or more detectors 4/sensors) allows, for the portion of log consisting of the set of said sections, the same information which could be obtained with a conventional rotary tomograph with resolution in the axial direction equal to the length of the basic volumes.

In the preferred embodiments which use a plurality of detectors, the detectors are positioned side by side parallel with the main axis of extension, and at a distance such that between the various readings there is a reciprocal $$\text{distance } D = P \cdot K/M.$$

where M is the number of detectors used.

In this way, it is possible to take maximum advantage of the readings and to minimize the volume of the basic volume used for the reconstructions. This is because each point of the basic volume is detected only once by a single detector.

As already indicated, the data acquired in the various readings can be processed using conventional tomographic reconstruction methods, whether precise or approximate. Said methods, being of the known type, are not described in detail herein.

To summarize, the embodiment according to this invention allows a good resolution to be maintained in the directions transversal to the main axis of extension of the wooden element 1, although drastically reducing the resolution along the axis itself. However, that guarantees optimum reconstructability of all of those features which remain unchanged over significant axial portions of the wooden element 1, such as growth rings, cracks, decaying zones, sapwood, bark, etc.

As an example of the good results obtainable, FIGS. 7 to 12 show a comparison of a reconstruction possible using the method according to this invention and a reconstruction obtained with a conventional rotary tomograph.

In said example, three different types of logs were initially subjected to a conventional rotary tomographic scan, that is to say, for each cross-section of the log, a plurality of readings according to different angles.

Once that information was obtained, it was possible to simulate the result obtainable with the method according to this invention without the need for a prototype. It was enough to extract from the set of readings only those which would be obtained with a tomograph operated according to this invention, and to reconstruct the tomographic image with only those readings.

In particular, the readings were selected in such a way that they would correspond with those obtainable using a generator positioned 95 cm from the centre of rotation (main axis of extension of the log) using five linear detectors 4 (each comprising a row of 7 mm wide sensors) positioned 150 cm from the generator, parallel with each other and spaced in such a way that they are separated from each other by 20 cm parallel with the axis of rotation.

It was also assumed that the generator and the detectors 4 would rotate at 2 revolutions/second, at the same time having the log fed axially at a speed of 2 meters/second.

Consequently, the simulated system had a pitch P of one meter and a detection width L=7 mm (the sum of the various detection lengths corresponding to 35 mm). Assuming that K=1 the parameters Y and X both had the value 28.5.

Figure 7:
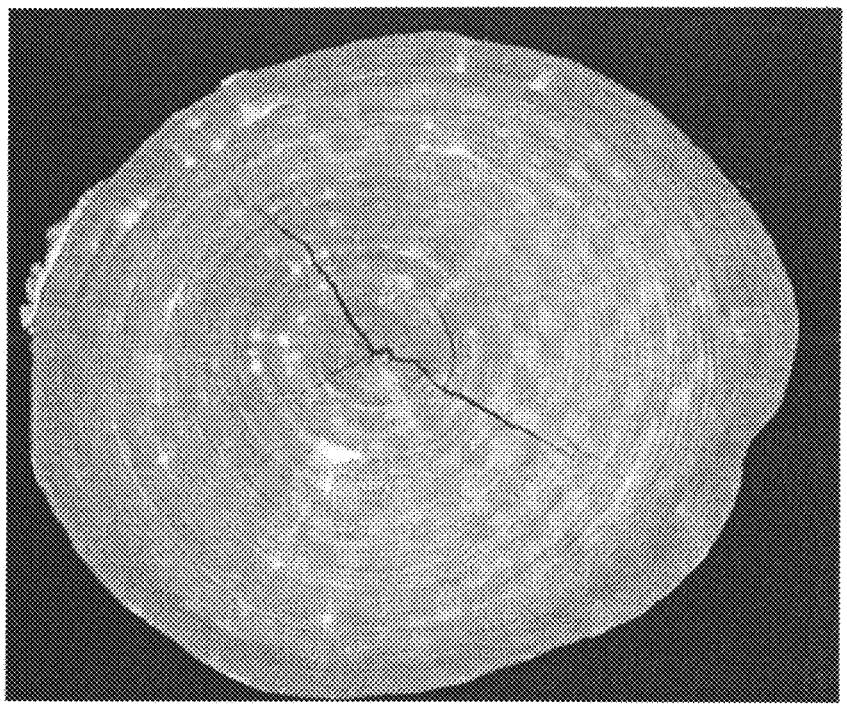
FIGS. 7 to 12 show a comparison of the results which can be obtained using the method according to this invention (FIGS. 8, 10 and 12) and those obtainable with a conventional rotary tomograph (FIGS. 7, 9 and 11).
Figure 8:
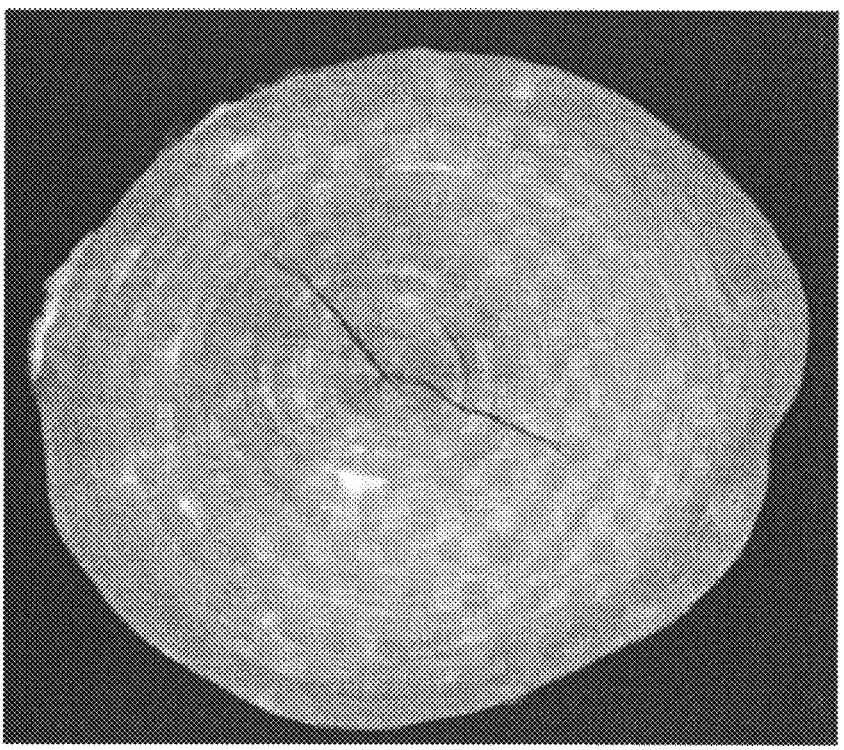
Figure 9:
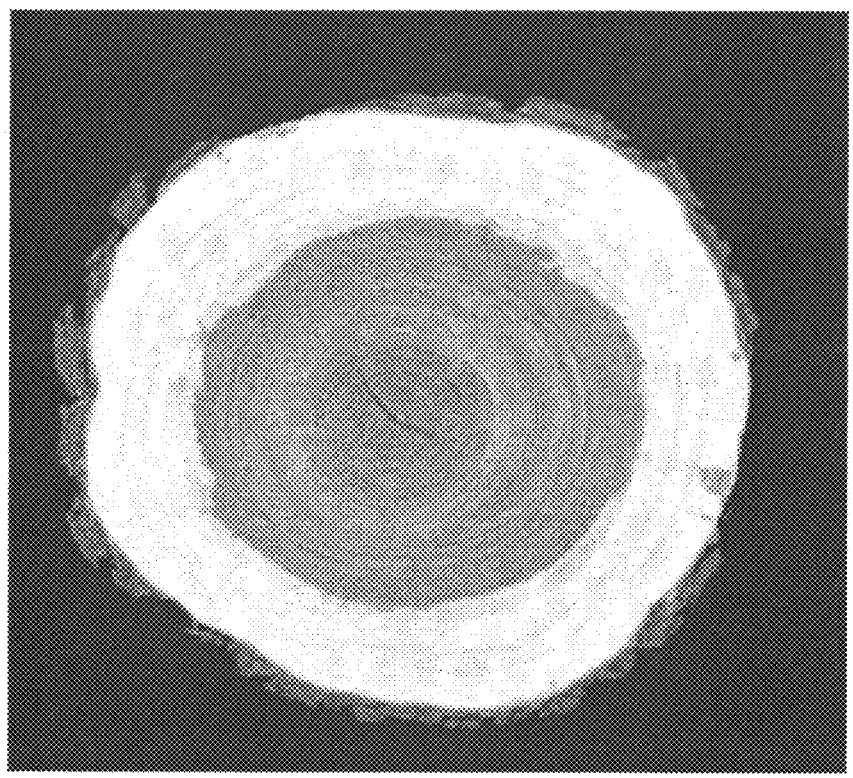
Figure 10:
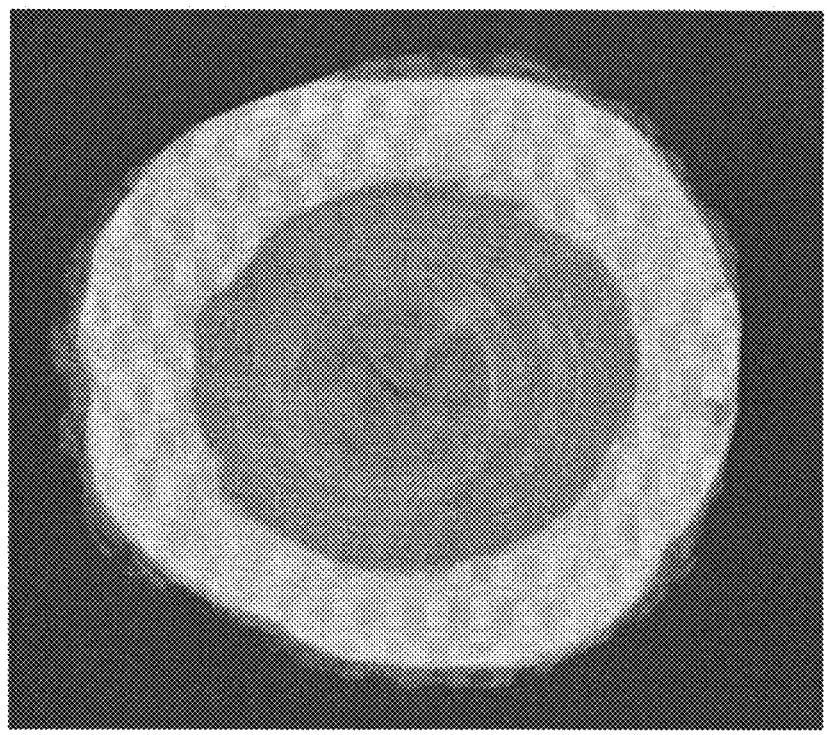
Figure 11:
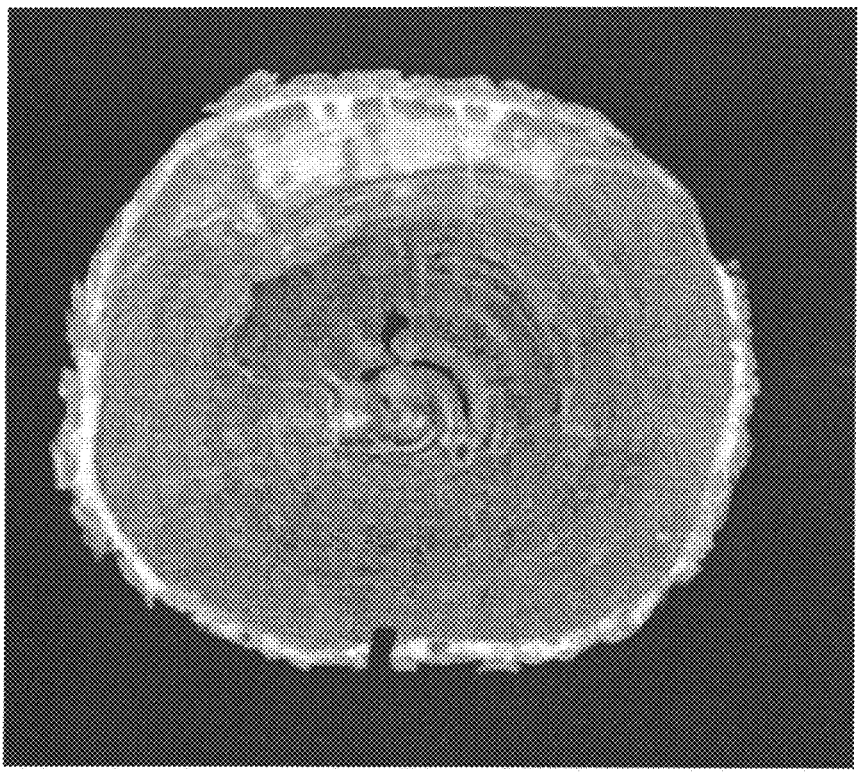
Figure 12:
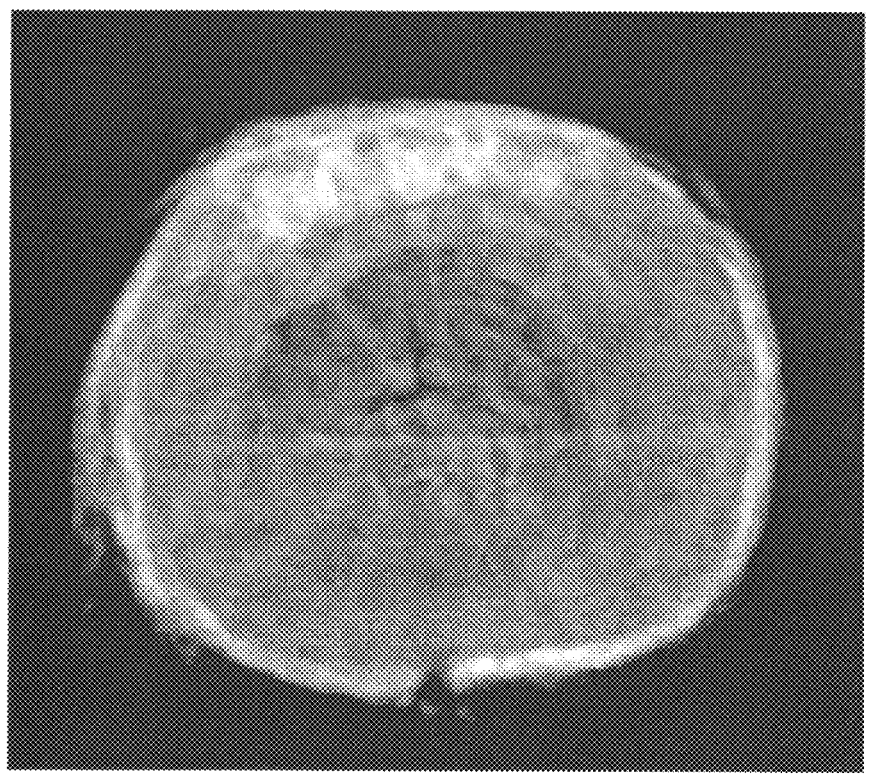

FIGS. 7 and 8 relate to the identification of a crack in a cherry-wood log. FIGS. 9 and 10 relate to the identification of a crack and distinguishing between bark/sapwood/heartwood on a pinewood log. FIGS. 11 and 12 relate to the identification of a decaying zone in a fir-wood log.

As can be seen, although more "out of focus" the results obtainable are very precise as regards the axial features.

This invention therefore brings important advantages.

First, thanks to this invention it was possible to provide a method capable of high speed detection of defects and other axial features which could not be detected using conventional systems operating with fixed sources, but which at the same time has production and operating costs comparable with those of fixed source systems.

It should also be noticed that this invention is relatively easy to produce and that even the cost linked to implementing the invention is not very high.

The invention described above may be modified and adapted in several ways without thereby departing from the scope of the inventive concept.

Moreover, all details of the invention may be substituted with other technically equivalent elements and in practice all of the materials used, as well as the shapes and dimensions of the various components, may vary according to requirements.

The invention claimed is:

1. A method for scanning the internal quality of wooden elements (1) having a main direction of extension, such as logs or planks, comprising the operating steps of taking a wooden element (1) having a main direction of extension identifiable with a main axis of extension of it;

irradiating the wooden element (1) with at least one beam (3) of electromagnetic radiation in one or more directions of irradiation which are transversal to the main axis of extension;

creating a relative helicoidal movement between the wooden element (1) and the beam (3) of electromagnetic radiation, the relative movement having a first component which is a translation substantially parallel with the main axis of extension of the wooden element (1) and a second component which is a rotation substantially about the wooden element (1);

during said movement, for a plurality of separate reciprocal positions of the wooden element (1) and the beam (3), using at least one detector (4) comprising a plurality of sensors to detect the residual intensity of at least part of the electromagnetic radiation which passed through the wooden element (1) and which, parallel with the main axis of extension, affects the wooden element (1) for a detection length (L); and reconstructing the internal structure of the wooden element (1) based on processing of the intensities detected for each reciprocal position;

the method being characterized in that the step of creating a relative movement between the beam (3) and the wooden element (1) is carried out in such a way that the helix formed by the relative movement has a pitch P equal to Y times the sum of the detection lengths (L) of all of the detectors used, where $Y \geq 5$, and also being characterized in that the step of reconstructing the internal structure of the wooden element (1), at a cross-section of its main axis of extension, is at least implicitly carried out by dividing the volume of the wooden element (1) at the section to be reconstructed, into a plurality of basic volumes assumed to have constant density, each having a structure which is extended parallel with the main axis of extension in such a way that the dimension of each basic volume along the main axis of extension is equal to at least X times the detection length (L) of each detector used, where $X \geq 5$.

2. The method according to claim 1, characterized in that the reconstructing step is at least implicitly carried out by considering for each basic volume a plurality of readings taken through portions of the wooden element (1) which are at least partly separate and distributed relative to each other along the main axis of extension.

3. The method according to claim 1, characterized in that the irradiating step involves sending a plurality of beams (3) of electromagnetic radiation through the wooden element (1), and in that the detecting step is carried out, for each reciprocal position, for each of the beams (3) of electromagnetic radiation.

4. The method according to claim 3, characterized in that the electromagnetic radiation of the various beams (3) which are detected after passing through the wooden element (1), overall axially affects the wooden element (1) for said detection length (L).

5. The method according to claim 3, characterized in that the irradiating step involves forming a plurality of beams (3) which are parallel with each other.

6. The method according to claim 5, characterized in that the beams (3) are generated in the same direction.

7. The method according to claim 6, characterized in that the detecting step is carried out using a plurality of detectors (4) which are positioned side by side and spaced out parallel with the main axis of extension.

8. The method according to claim 3, characterized in that the irradiating step involves forming a plurality of beams (3) diverging from a single emitter (5).

9. The method according to claim 8, characterized in that the diverging beams (3) are created by irradiating the wooden element (1) with a cone- or pyramid-shaped macro-beam (6).

10. The method according to claim 8, characterized in that the detecting step is carried out using a plurality of detectors (4) which are positioned side by side and spaced out parallel with the main axis of extension.

11. The method according to claim 3, characterized in that the beams (3) are generated in such a way that they are angled according to different angular positions relative to the main axis of extension, and also being characterized in that the step of detecting each beam (3) is carried out using a relative detector (4), the detectors (4) being located in various angular positions relative to the main axis of extension.

12. The method according to claim 3, characterized in that each beam (3) is generated in such a way that it completely or partly affects the wooden element (1), transversally to the main axis of extension.

13. The method according to claim 3, characterized in that the relative movement is generated by feeding the wooden element (1) in a feed direction parallel with the main axis of extension and by rotating each beam (3) and each detector (4) about the wooden element (1), each beam (3) and each detector (4) otherwise being held stationary relative to the ground.

14. The method according to claim 3, characterized in that the step of creating a relative movement between the beam (3) and the wooden element (1) is carried out in such a way that $Y \geq 10$.

15. The method according to claim 1, characterized in that each beam (3) is generated in such a way that it completely or partly affects the wooden element (1), transversally to the main axis of extension.

16. The method according to claim 15, characterized in that the relative movement is generated by feeding the wooden element (1) in a feed direction parallel with the main axis of extension and by rotating each beam (3) and each detector (4) about the wooden element (1), each beam (3) and each detector (4) otherwise being held stationary relative to the ground.

17. The method according to claim 15, characterized in that the step of creating a relative movement between the beam (3) and the wooden element (1) is carried out in such a way that $Y \geq 10$.

18. The method according to claim 1, characterized in that the relative movement is generated by feeding the wooden element (1) in a feed direction parallel with the main axis of extension and by rotating each beam (3) and each detector (4) about the wooden element (1), each beam (3) and each detector (4) otherwise being held stationary relative to the ground.

19. The method according to claim 18, characterized in that the step of creating a relative movement between the beam (3) and the wooden element (1) is carried out in such a way that $Y \geq 10$.

20. The method according to claim 1, characterized in that the step of creating a relative movement between the beam (3) and the wooden element (1) is carried out in such a way that $Y \geq 10$.

* * * * *